United States Patent [19]

Mimoun

[11] 4,250,121

[45] Feb. 10, 1981

[54] CATALYTIC OXIDATION OF ALCOHOLS WITH MOLECULAR OXYGEN TO FORM CARBONYL COMPOUNDS

[75] Inventor: Hubert Mimoun, Rueil-Malmaison, France

[73] Assignee: Institut Francais du Petrole, Rueil-Malmaison, France

[21] Appl. No.: 41,855

[22] Filed: May 24, 1979

[30] Foreign Application Priority Data

May 24, 1978 [FR] France ................ 78 15671

[51] Int. Cl.³ ................ C07C 45/38; C07C 45/39
[52] U.S. Cl. ................ 568/431; 568/360; 568/402; 568/432; 568/471
[58] Field of Search ............ 568/594; 260/603 C, 260/600, 600 R, 596, 599, 594

[56] References Cited

U.S. PATENT DOCUMENTS

| | | | |
|---|---|---|---|
| 3,479,403 | 11/1969 | MacLean | 260/596 X |
| 3,836,553 | 9/1974 | Fenton | 260/596 X |
| 4,117,016 | 9/1978 | Hughes | 260/603 C X |

FOREIGN PATENT DOCUMENTS

| | | | |
|---|---|---|---|
| 823514 | 11/1959 | United Kingdom | 260/596 |
| 1530447 | 11/1978 | United Kingdom | 260/596 |

*Primary Examiner*—Bernard Helfin
*Attorney, Agent, or Firm*—Millen & White

[57] ABSTRACT

Carbonyl compounds are manufactured by oxidizing alcohols or polyalcohols with molecular oxygen in the presence of a catalyst which comprises ruthenium salts or complexes associated with copper or iron salts or complexes.

16 Claims, No Drawings

CATALYTIC OXIDATION OF ALCOHOLS WITH MOLECULAR OXYGEN TO FORM CARBONYL COMPOUNDS

This invention relates to a process for manufacturing aldehydes or ketones by oxidation of primary or secondary alcohols in liquid phase in the presence of a catalyst consisting of two associated transition metal salts or complexes, the metal of one of the two salts being ruthenium.

The general scheme of the reaction is:

$$R_1-\underset{R_2}{\underset{|}{C}}HOH + \tfrac{1}{2} O_2 \longrightarrow R_1-\underset{R_2}{\underset{\|}{C}}=O + H_2O$$

wherein $R_1$ is a hydrocarbon radical and $R_2$ a hydrocarbon radical in the case of a secondary alcohol or a hydrogen atom in the case of a primary alcohol.

The process of the invention uses as catalyst system two associated salts or organometallic complexes (A) and (B) of the general formulas:

$$(A) = M_1 X_n L_m$$

$$(B) = M_2 Z_p L'_q$$

In the salt or complex (A), $M_1$ is ruthenium, X is an anionic group such as halogen, sulfate, nitrate, carboxylate, perchlorate, tetrafluoborate and acetylacetonate, n is an integer selected from 2 and 3, L is a ligand consisting of a water molecule or an organic compound such as a phosphine, an arsine or a diolefin; m is an integer selected from 1, 2, 3 or 6, or is zero.

By way of non limitative examples of compounds (A), the following ruthenium salts or complexes may be mentioned:

ruthenium chlorides, bromides and iodides of the formula $RuX_3 \cdot mH_2O$ (X=Cl, Br, I);

ruthenium trifluoracetate;

the complexes $Ru X_2L_3$ where X=Cl, Br, I and L is a phosphine, arsine or stibine, for example, triphenylphosphine and triphenylarsine;

the polymeric complexes $[RuCl_2(diolefin)]_n$ where the diolefin is, for example, norbornadiene (NBD) or 1,5-cyclooctadiene.

In the salt or complex (B) to be used jointly with the complex (A):

$M_2$ is a transition metal selected from iron and copper,

Z is an anionic group such as halogen, carboxylate, sulfate, nitrate, perchlorate or tetrafluoborate, p is an integer selected from 1, 2 and 3, L' is a ligand, consisting of a water molecule or an organic molecule such as, for example, dimethylformamide, hexamethyl-phosphorotriamide or dimethyl sulfoxide, q is an integer from 1 to 6 or is zero.

By way of non-limitative examples of the compounds B, there can be mentioned:

the iron or copper perchlorates, nitrates, sulfates, fluoborates and trifluoroacetates, the copper and iron halides of the formula $MZ_p \cdot qH_2O$ where Z is chlorine or bromine and M is iron or copper, p being an integer selected from 2 and 3 and q is zero or an integer from 1 to 6, complexes, such as $Cu(ClO_4)_2 \cdot 4L'$; $Cu(NO_3)_2 \cdot 4L'$; $Fe(ClO_4)_2 \cdot 4L'$; $Fe(NO_3)_3 \cdot 4L'$, where L' is a ligand such as dimethylformamide, hexamethylphosphorotriamide and dimethyl-sulfoxide.

The molar ratio B/A of the two catalyst constituents is usefully between 0.5 and 20, preferably between 1 and 5.

Further to the above metal constituents (A) and (B), it is often advantageous, in order to improve the reaction selectivity, to use a third constituent of basic character, such as a tertiary amine of the formula NR'R''R''', where R', R'' and R''', identical or not, are alkyl, aryl, aralkyl or alkylaryl groups with 1–20 carbon atoms per molecule. Non-limitative examples thereof are triethylamine, triethanolamine and N-methyl morpholine.

An alkaline alcoholate such as sodium or potassium ethylate, isopropylate or tertio-butylate may also be added as the constituent of basic character. This alcoholate may also be obtained by adding sodium or potassium metal to the alcohol used as substrate. As a rule, the molar rotio of the basic component to ruthenium is between 1 and 20; however the preferred ratio to be used is between 1 and 4.

This invention concerns the oxidation of alcohols or polyalcohols selected from the aliphatic, cycloaliphatic, arylaliphatic and alkylarylaliphatic alcohols and polyalcohols with 2 to 30 carbon atoms per molecule. These alcohols or polyalcohols may be primary or secondary and may include one or more functional groups such as the nitro, nitrile, ether oxide, ester and acid groups. Non-limitative examples thereof are: ethanol, n-propanol, isopropanol, butanol, isobutanol, 2-butanol, 1,2 or 3-pentanols, 1,2 or 3-hexanols, 1,2,3 or 4-octanols, cyclopentanol, cyclohexanol, cinnamyl alcohol, 1,6-hexane diol and citronellol. Benzyl alcohol and benzyl alcohols substituted with alkyl, nitro, cyano, hydroxyl or ether groups may also be oxidized according to this invention. For example, benzyl alcohols substituted with phenoxy groups in the ortho, meta or para positions may be oxidized to the corresponding phenoxybenzaldehydes. These compounds are useful intermediates in the synthesis of pyrethroidic insecticides.

The solvent for the reaction is generally the alcohol substrate itself. It can also be operated in a solvent such as an aliphatic or aromatic hydrocarbon, a chlorinated solvent, a ketone, a linear or cyclic ether, a nitrile such as acetonitrile or a basic solvent such as dimethylformamide or hexamethylphosphorotriamide.

The aldehyde or ketone obtained according to the invention by oxidation of the corresponding primary or secondary alcohol or polyalcohol reacts often with the latter to yield the corresponding acetal or ketal according to the balanced scheme:

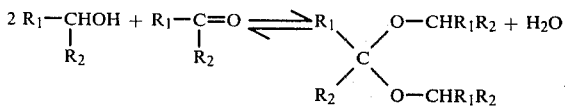

This balance may be displaced in favor of the carbonyl derivative whenever the latter is continuously discharged from the reactor; this is advantageously obtained by oxidizing at a temperature substantially close to the boiling temperature of the carbonyl derivative which is more volatile than the starting alcoholic substrate and which can be discharged continuously, in the gas form, from the reaction medium.

The reaction temperature is generally from 20° to 180° C., particularly from 50° to 150° C.

The oxidizing gas may consist of molecular oxygen pure or diluted with nitrogen or with any inert gas. The oxygen partial pressure is from 0.1 to 20 bars. The molar ratio of (A) to the alcohol or polyalcohol is from 1/10,000 to 1/10 and preferably from 1/1,000 to 1/10.

The invention is illustrated by the following examples:

EXAMPLE No. 1

A heat-insulated reactor is charged with 50 cc (0.5 mole) of n-butanol, then 1 millimol of ruthenium chloride ($RuCl_3.3H_2O$) and 4 millimol of copper (II) perchlorate. The temperature is raised to 80° C. The free space within the reactor is then fed with free oxygen to attain a total pressure of 1.2 bars. Stirring within the reactor is effected by means of a magnetic stirrer. It is observed that the oxygen pressure decreases in the reactor; that oxygen pressure is then maintained at 1.2 bar by permanent oxygen supply.

After a 4 hour reaction, 30 millimol oxygen have been absorbed and it is found by chromatographic analysis that 10 millimol.butanal, 30 millimol. 1,1-dibutoxy butane and 1.5 millimol.butyric acid have been formed.

EXAMPLES 2 to 8

The following examples show (see table I) that various bimetallic systems (A) and (B) may be used to oxidize n-butanol to butyraldehyde (butanal). The operation is as in example 1. The temperature is 80° C., the n-butanol volume is 50 cc (0.5 mole); the oxygen pressure is 1.2 bars; the reaction time is 4 hours. The following table, which illustrates these examples, shows that ruthenium, when used as chloride and associated with copper as perchlorate [$Cu(ClO_4)_2(HMPT)_4$] has the optimum catalytic activity.

TABLE I

| examples | Complex A 1 m. moles | Complex B 4 m. moles | Resultant butanal m. moles | 1,1-di-butoxy butane m. moles |
|---|---|---|---|---|
| 2 | $RuCl_3 . 3H_2O$ | absence | 1.6 | 0.89 |
| 3 | $RuCl_3 . 3H_2O$ | $Cu(ClO_4)_2(HMPT)_4$ | 14 | 32 |
| 4 | $RuCl_3 . 3H_2O$ | $CuCl_2 . 2H_2O$ | 5.1 | 1.4 |
| 5 | $RuCl_3 . 3H_2O$ | $Cu(NO_3)_2 . 3H_2O$ | 2 | 7.9 |
| 6 | $[RuCl_1(NBD)]_n$ | $Cu(ClO_4)_2(HMPT)_4$ | 3 | 8.3 |
| 7 | $PdCl_2$ | $Cu(ClO_4)_2(HMPT)_4$ | 1.6 | 0.7 |

NBD = Norbornadiene,
HMPT = hexamethylphosphorotriamide

EXAMPLES 8 to 17

The following examples show (Table II) that the $RuCl_3.3H_2O$—$Cu(ClO_4)_2(HMPT)_4$ system, where HMPT designates hexamethylphosphorotriamide, is a catalyst for oxidizing primary and secondary alcohols to the corresponding aldehydes and ketones. The operation is as in example 1; the temperature is 60° C., the alcohol volume is 50 cc, the oxygen pressure is 1.2 bars and the reaction time is 4 hours; 1 m. mole $RuCl_3.3H_2O$ and 4 m.mole $Cu(ClO_4)_2(HMPT)_4$ have been used.

TABLE II

| Example | Starting alcohol | Resultant aldehyde or ketone m.moles | Resultant acetal or ketal m. moles |
|---|---|---|---|
| 8 | ethanol | ethanal 4.5 | 15.2 |
| 9 | n-propanol | propanal 7.9 | 17.5 |
| 10 | 1-butanol | butanal 8 | 20.5 |
| 11 | 1-hexanol | hexanal 11 | 16 |
| 12 | 1-octanol | octanal 5 | 13 |
| 13 | 2-butanol | butanone-2 7 | 12 |
| 14 | benzyl alcohol | benzaldehyde 14 | — |
| 15 | cinnamyl alcohol | cinnamaldehyde 25 | — |
| 16 | cyclohexanol | cyclohexanone 20 | — |
| 17 | 3-phenoxy-benzylic alcohol | 3-phenoxy-benzaldehyde 10 | — |

EXAMPLES 18 and 19

The following examples illustrate (Table III) the favorable effects observed on the reaction velocity and selectivity when adding a constituent of basic character to the ruthenium-copper catalytic system.

The operation is as in example 1. The temperature is 80° C., the oxygen pressure 1.2 bars, the n-butanol volume 50 cc. 1 m.mole of $RuCl_3.3H_2O$ and 4 m.moles $Cu(ClO_4)_2(HMPT)_4$ have been used.

It is found that, when adding a sodium alcoholate in low proportion, the subsequent reaction of oxidizing butanal to butyric acid is avoided.

TABLE III

| Example | Constituent | Resultant butanal m.moles | dibutoxy-butane | Butyric acid |
|---|---|---|---|---|
| 1 (comparison) | absence | 14 | 32 | 1.5 |
| 18 | potassium tertiobutylate 2 m.moles | 18 | 45 | un-detected |
| 19 | sodium methylate 2 m.moles | 15 | 40 | un-detected |

EXAMPLE 20

500 cc (5 mol.) 1-butanol, 10 millimoles ruthenium chloride and 40 millimoles $Cu(ClO_4)_2(HMPT)_4$ is introduced into a heat-insulated reactor at 90° C., said reactor being provided with a magnetic stirrer and surmounted with a heat-insulated packing column connected to a water-cooler opening over a collecting vessel. Air is then bubbled through the liquid at a constant rate of 200 l/hour.

After one hour there is collected in a vessel: 0.12 moles butanal as well as n-butanol and water. n-Butanal is then supplied to the reactor through a pump at a constant rate of 0.4 mole/h and 0.1 mole/h butanal is discharged into the collecting vessel, together with butanol and water. The distillation of the resulting mixture yields butyraldehyde and unreacted butanol which is recycled.

EXAMPLE 21

Example 3 is repeated, while replacing ruthenium chloride with ruthenium trifluoroacetate, the other conditions of the example being unchanged. 13.8 m.moles butanal and 32 m.moles 1,1-dibutoxybutane have been formed.

EXAMPLE 22

Example 18 is repeated, while using 1 m.mole ruthenium trifluoroacetate instead of 1 m.mole ruthenium trichloride. 18 m.moles butanal and 46 m.moles dibutoxybutane have been formed. No butyric acid is present.

What is claimed is:

1. A process for producing an aldehyde or ketone, which comprises contacting a primary or secondary alcohol or polyalcohol having from 2 to 30 carbon atoms per molecule with a sufficient partial pressure of molecular oxygen at a sufficient temperature in the presence of a catalyst system comprising:
   (A) a ruthenium salt or complex having the formula $RuX_nL_m$; wherein X is halogen, sulfate, nitrate, carboxylate, perchlorate, tetrafluoborate or acetylacetonate; n is the integer 2 or 3; L is a water, a phosphine, an arsine or a diolefin ligand; and m is the integer 0, 1, 2, 3 or 6; and
   (B) a copper or iron salt or complex having the formula $MZ_pL'_q$; wherein M is copper or iron; Z is halogen, sulfate, nitrate, carboxylate, perchlorate or tetrafluoborate; p is the integer 1, 2 or 3; L is a water, dimethylformamide, hexamethylphosphorotriamide or dimethylsulfoxide ligand; and q is an integer from 0 to 6.

2. A process according to claim 1, wherein X is chloride, bromide, iodide, or trihaloacetate; n is 3; and L is water.

3. A process according to claim 1, wherein Z is chloride, bromide, iodide, trifluoroacetate or perchlorate; and p is 2 or 3.

4. A process according to claim 3, wherein L' is water, dimethylformamide or hexamethylphosphoramide; and q is 2 or 4.

5. A process according to claim 1, wherein the reaction is effected at a temperature of from 20° to 180° C., the molar ratio of the catalyst component (A) to the alcohol or polyalcohol being from 1/10,000 to 1/10 and the molar ratio (B)/(A) of the catalyst components (A) and (B) being from 0.5 to 20.

6. A process according to claim 5, wherein an alkaline alcoholate or a tertiary amine is added to improve the reaction selectivity, the molar ratio of the amine or alcoholate to ruthenium being from 1 to 20.

7. A process according to claim 5, wherein benzyl alcohol or benzyl alcohols substituted with phenoxy groups in the ortho, meta or para position are oxidized to the corresponding benzaldehydes.

8. A process according to claim 6, wherein the molar ratio of the amine or alcoholate to ruthenium is from 1 to 4.

9. A process according to claim 5, wherein the molar ratio (B)/(A) is from 1 to 5.

10. A process according to claim 1, wherein the oxidation is conducted at a temperature substantially close to the boiling point of the resultant aldehyde or ketone.

11. A process according to claim 8, wherein component (A) is ruthenium trifluoroacetate, $RuCl_3$ or $RuCl_3.3H_2O$ and component (B) is copper perchlorate or $Cu(ClO_4)_2(HMPT)_4$ where HMPT is a hexamethylphosphorotriamide ligand.

12. A process according to claim 6, wherein the tertiary amine has the formula NR'R"R"', wherein R', R" and R"' are each independently alkyl, aryl, aralkyl or alkylaryl groups having from 1 to 20 carbon atoms.

13. A process according to claim 6, wherein the tertiary amine is triethylamine, triethanolamine or N-methylmorpholine.

14. A process according to claim 6, wherein the alkaline alcoholate is sodium or potassium ethylate, isopropylate or tertio-butylate.

15. A process according to claim 6, wherein the alkaline alcoholate is obtained by adding sodium or potassium metal to the alcohol reactant.

16. A process according to claim 5, wherein the oxygen partial pressure is from 0.1 to 20 bars.

* * * * *